(12) United States Patent
Morgan

(10) Patent No.: US 6,200,551 B1
(45) Date of Patent: Mar. 13, 2001

(54) TREATMENT FOR DRY MOUTH EMPLOYING CARBAMIDE PEROXIDE

(76) Inventor: Susan Ann Morgan, 1550 Bay St., Apt. #332, San Francisco, CA (US) 94123-1761

(*) Notice: Subject to any disclaimer, the term of this patent is extended or adjusted under 35 U.S.C. 154(b) by 0 days.

(21) Appl. No.: 09/492,356

(22) Filed: Jan. 27, 2000

(51) Int. Cl.⁷ .............................. A61K 7/20; A61K 7/16; A61K 33/10
(52) U.S. Cl. ......................... 424/53; 424/54; 424/613; 424/616; 514/588; 514/714; 514/901
(58) Field of Search ...................... 424/53, 54, 613, 424/616; 514/901, 588, 714

(56) References Cited

U.S. PATENT DOCUMENTS

| | | | |
|---|---|---|---|
| 2,430,450 | * 11/1947 | Brown et al. | 167/58 |
| 3,657,413 | * 4/1972 | Rosenthal et al. | 424/81 |
| 4,438,100 | * 3/1984 | Balslev et al. | 424/104 |
| 5,039,515 | * 8/1991 | Korf | 424/53 |
| 5,540,913 | * 7/1996 | Turner | 424/53 |
| 5,693,334 | * 12/1997 | Miskewitz | 424/440 |

* cited by examiner

*Primary Examiner*—Diana Dudash
*Assistant Examiner*—Shahnam Sharareh
(74) *Attorney, Agent, or Firm*—Goldstein & Canino

(57) ABSTRACT

A treatment for xerostomia, employing a composition having the active ingredient of carbamide peroxide. The carbamide peroxide compound contains urea and hydrogen peroxide. The hydrogen peroxide remains stable until the carbamide peroxide is applied to the mouth and contacts the water inherent therein. On contact, the hydrogen peroxide is freed from the urea, allowing the hydrogen peroxide to react within the mouth. The resulting chemical and mechanical reaction stimulates saliva within the mouth and thereby relieves the symptoms of xerostomia.

3 Claims, No Drawings

TREATMENT FOR DRY MOUTH EMPLOYING CARBAMIDE PEROXIDE

BACKGROUND OF THE INVENTION

The invention relates to the use of hydrogen peroxide for the treatment of xerostomia (a medical condition commonly known as "dry mouth"). More specifically, the invention relates to the use of carbamide peroxide, a stable compound of hydrogen peroxide and urea, for relieving the symptoms and side-effects of xerostomia.

Saliva is a complex mixture of fluids, proteins, enzymes, and electrolytes that are produced by the salivary glands which surround the oral cavity, and is secreted into the mouth following appropriate stimulation of oral tissues. Secretion of saliva is regulated by the body's autonomic nervous system which permits involuntary secretion following an appropriate stimulus such as tasting or chewing food, smelling or thinking of food, or having any object within the mouth which stimulates the oral mucosa.

Xerostomia occurs when inadequate amounts of saliva are secreted into the mouth, preventing adequate lubrication of the oral cavity and resulting in an uncomfortable oral sensation and difficulty with speaking and swallowing. Severe cracking of the tongue can also result. In addition to the primary role of lubricating the oral cavity during conversation and eating, saliva also limits growth of bacteria that can cause tooth decay and oral infections, promotes digestion of food, and acts as a protective barrier against demineralization of tooth enamel.

Xerostomia can result from either decreased production of saliva within the glands and/or diminished secretion of saliva from the glands following autonomic stimulation. It is most commonly caused as an unwanted side effect of many classes of prescription medications including anticholinergics, antispasmodics, antihypertensives, antidepressants, anticonvulsants, pain killers, anti-rejection drugs, and antipsychotics, as well as over-the-counter decongestants and antihistamines. These classes of drugs either directly inhibit saliva production within the glands or inhibit its secretion into the mouth by inhibiting the autonomic nervous system.

Xerostomia can also occur during states of elevated stress, anxiety, depression, with certain endocrine diseases such as hypothyroidism, during chemotheraphy, and with autoimmune disorders such as Sjogren's syndrome. Additionally, people who have had radiation therapy to the neck, traumatic injury to the neck, or neck surgery may also develop xerostomia due to destruction of the glands by the therapeutic radiation dose, or direct injury of the gland and its controlling autonomic nerves. Xerostomia is increasingly common among people of advancing age.

Typical treatment considerations for xerostomia have involved supportive and replacement therapies to restore oral moisture, as well as pharmacologic agents to stimulate the body's own saliva production.

Supportive therapy incorporates behavior and dietary modifications to keep the mouth moist throughout the day to minimize discomfort. Such strategies include frequent drinks of water, avoiding liquids with caffeine or sugar, avoiding alcohol and tobacco products, avoiding spicy or acidic foods, and following a regular daily dental hygiene program.

Replacement therapy incorporates oral administration of exogenous saliva-like compounds in order to replenish lost moisture, fluids and enzymes in the oral cavity, while introducing an appropriately viscous compound that aids in the mechanics of speaking and swallowing. Reference to current medical literature reveals several saliva replacement products.

BIOTENE, produced by Laclede Inc., is a salivary enzyme replacement system in a toothpaste form that contains the active ingredient found in toothpaste (sodium monofluorophosphate) and the major enzymes found in saliva (lactoperoxidase, thiocyanate and glucoseoxidase). BIOTENE primarily functions to prevent the damage caused by harmful bacteria that can accumulate in the mouth when inadequate amounts of saliva are present. In toothpaste form it is less effective at long-term relief of the classic symptoms of dry mouth but is also available in mouthwash, chewing gum, and oral gel (ORALBALANCE) preparations which include oral moisturizing agents that are more effective in longer duration of symptom relief.

SALIX, produced by Reach4Life Enterprises, is available in tablet form and contains sorbitol, polyethylene glycol, malic acid, hydrogenated cottonseed oil, sodium citrate, dicalcium phosphate, citric acid, silicon dioxide, and carboxy methylcellulose. It acts as a temporary semi-viscous saliva substitute to improve the mechanics of speaking and swallowing but does little to inhibit oral bacteria responsible for tooth decay.

SALAGEN, commonly known as pilocarpine hydrochloride, produced by MGI Pharma, Inc., is a pharmacologic agent that is indicated and approved for treatment of xerostomia in persons who have undergone radiation therapy to the neck and in persons with Sjogren's syndrome. Available in tablet form, SALAGEN is a cholinergic agent that is effective in pharmacologically increasing secretions from the salivary glands thereby improving the symptoms of xerostomia. Salagen™ however acts on all exocrine glands in the body and also increases secretions from the skin, eyes, pancreas, intestines, and lungs with unwanted and sometimes deleterious side-effects. Additionally, pilocarpine can cause decreased visual acuity and cardiovascular collapse with serious and possibly life-threatening consequences.

It is evident that current supportive and replacement therapies for treating xerostomia (BIOTENE and SALIX) are temporary and do little to directly stimulate the body to produce and secrete more natural saliva. Current pharmacologic therapies (SALAGEN) which do increase the body's natural saliva production also cause unwanted increased secretions in other organs and can have serious side-effects. The current invention describes a compound that relieves the symptoms of xerostomia by causing the salivary glands to produce and secrete natural saliva into the oral cavity without the serious and lifestyle-limiting side effects of current pharmacologic agents.

While the previously discussed therapies are suitable for their particular purposes, they are not suitable for the purposes of the current invention which employs an over-the-counter drug compound to increase natural saliva production and secretion in persons with xerostomia without the serious side-effects associated with currently available prescription medication.

SUMMARY OF THE INVENTION

It is an object of the invention to provide a system which effectively treats xerostomia, and relieves the discomfort associated therewith. Accordingly, the current invention relates to the use of carbamide peroxide as a salivary replacement system to stimulate the body's own production of saliva by an oxygen-releasing biochemical foaming process within the mouth. In addition, the composition according to the present invention can act as a oral moisturizer and a saliva substitute.

It is a further object of the invention to provide a system which is known to be safe, so that it is approved for use in the manner of the present invention. Accordingly, the active ingredient of the invention is carbamide peroxide. Carbamide peroxide is a stable organic compound of urea and hydrogen peroxide which is currently employed in several over-the-counter drug remedies for removal of ear wax (MURINE, DEBROX), oral debriding and cleansing agents (GLYOXIDE, ORAJEL) and tooth whitening agents (PLATINUM OVERNIGHT). Carbamide peroxide has been fully described in FDA drug monographs listed in the Federal Register (21 CFR Parts 201, 344, 353, 356, and 369) for over-the-counter agents.

It is a further object of the invention to provide a system which is both capable of stimulating saliva production, but is also capable of clearing some mechanical blocking of the salivary ducts. Accordingly, the effervescent reaction of the carbamide peroxide within the mouth is capable of clearing distal blockages of the salivary ducts.

The invention is a treatment for xerostomia, employing a composition having the active ingredient of carbamide peroxide. The carbamide peroxide compound contains urea and hydrogen peroxide. The hydrogen peroxide remains stable until the carbamide peroxide is applied to the mouth and contacts the water inherent therein. On contact, the hydrogen peroxide is freed from the urea, allowing the hydrogen peroxide to react within the mouth. The resulting chemical and mechanical reaction stimulates saliva within the mouth and thereby relieves the symptoms of xerostomia.

To the accomplishment of the above and related objects the invention may be embodied in the form described in the accompanying specification. Attention is called to the fact, however, that the examples given are illustrative only. Variations are contemplated as being part of the invention, limited only by the scope of the claims.

DETAILED DESCRIPTION OF THE PREFERRED EMBODIMENTS

To accomplish the goals of the present invention, a composition is employed having the active ingredient of carbamide peroxide. Carbamide peroxide is a stable organic compound of urea and hydrogen peroxide.

Hydrogen peroxide is one of the most powerful oxidizing agents available and has been used extensively in wound cleaning applications. It is a mild irritant to mucous membranes such as oral tissues. However, for the purposes of the present invention, hydrogen peroxide by itself is too unstable. If applied directly to the mouth, it quickly and violently reacts, but ceases its action within a very short period of time. Ironically, when attempting to use ordinary hydrogen peroxide for the purposes the present invention, the mouth is left with a dry feeling.

However, when hydrogen peroxide is combined with urea in the form of carbamide peroxide, it remains in a stable form until contact with skin tissues and mucous membranes. Upon contact with skin and tissues carbamide peroxide releases hydrogen peroxide which actively destroys harmful bacteria within the mouth, removes decaying tissues and most importantly, stimulates saliva secretion. In addition, exuberant amounts of oxygen are released in a mechanical foaming action as part of the biochemical conversion of hydrogen peroxide to water and oxygen. Furthermore, this "foaming action" acts as a further mechanical stimulant to salivary gland stimulation and saliva secretion. Both the chemical and mechanical actions of carbamide peroxide stimulating the salivary glands apparently serve to reduce or eliminate the effects of xerostomia.

Because the hydrogen peroxide remains stable until it is released from the urea, the carbamide peroxide in effect becomes a "time releasing" agent for the hydrogen peroxide, and seems to continue releasing low levels of hydrogen peroxide for atleast twelve hours. Once applied to the mouth, the carbamide peroxide can be effective at reducing or eliminating xerostomia for several days. It is believed that the delayed or indirect release of hydrogen peroxide provides the effective longevity of the carbamide peroxide for the purposes of the present invention.

The present invention can further serve to enhance proper saliva release by clearing mechanical blockages or "stones" within the salivary ducts. The "foaming action" can serve to clear stones within the salivary ducts, but is especially effective at clearing distal stones and other forms of distal blockages.

Use of the present invention involves the oral application of the composition to a patient suffering from xerostomia. Immediately upon contact with skin tissues and mucous membranes, water inherent therein begins causing urea from the carbamide peroxide to split from the hydrogen peroxide. The hydrogen peroxide then causes a strongly mechanical reaction wherein oxygen is rapidly released, and minor irritation to oral tissues results. The reaction also causes stimulation of the salivary glands and subsequent relief from the symptoms of xerostomia.

According to a preferred embodiment, the composition is a mixture of 10 percent carbamide peroxide in glycerin. Of course, different strengths may be employed, the most suitable of which may be determined by empirical testing. Keeping the hydrogen peroxide stably within the carbamide peroxide compound prior to use involves keeping the carbamide peroxide isolated from water. Accordingly, the carbamide peroxide may be maintained in a glycerin suspension. The glycerin can act as a moisturizer to further aid the invention in its goal of being an oral moisturizer.

According to a preferred manner of usage, the composition is applied directly to the mouth of a person suffering from xerostomia using an applicator brush, such as a toothbrush. The composition is applied directly to the brush, and is preferably not mixed with toothpaste or any other substance. Once on the brush, the composition is applied to all interior surfaces of the mouth—the roof of the mouth, the tongue, under the tongue, the gums, the inside of the cheeks, etc. As all surfaces of the mouth are coated, the hydrogen peroxide is released, causing a chemical reaction to immediately commence. The effervescent action of the hydrogen peroxide is most pronounced immediately following application, but then apparently dies down to a slow, time-released reaction. It seems that the continuing reaction keeps the dry-mouth curing properties of the invention working for a considerable period of time. By the preferred manner of usage of the invention, the application process is completed approximately twice daily (every nine to twelve hours). However, one application of the carbamide peroxide composition can be effective at preventing dry mouth for several days.

The foregoing description of the system and the reasons for its effectiveness is presented as best known by the inventor at the time of application. Although the precise mechanism of the invention and the reasons for its effectiveness will be determined in greater detail at a later date following further study, the invention is not limited by those embodiments which are presently known and described herein. Variations of the invention, using the same principles of the present invention in light of future discoveries of the properties of the present invention and suitable chemical substitutions therefor are contemplated as being part of the present invention, limited only by the scope of the claims.

What is claimed is:

1. A method of treating xerostomia, comprising the steps of:

providing a composition consisting of carbamide peroxide and glycerin;

applying the composition to interior surfaces of the mouth of a patient suffering from xerostomia; and releasing hydrogen peroxide by the composition upon contact with the interior surfaces of the mouth.

2. The method of treating xerostomia as recited in claim 1, further comprising the step of:

repeatedly reapplying the composition to the interior surfaces of the mouth of said patient substantially every nine to twelve hours.

3. The method of treating xerostomia as recited in claim 2, wherein the step of applying the composition to interior surfaces of the mouth further comprises the steps of:

applying the composition to an applicator brush; and brushing the interior surfaces of the mouth with the applicator brush.

* * * * *